United States Patent
Lee et al.

(10) Patent No.: US 11,802,263 B2
(45) Date of Patent: Oct. 31, 2023

(54) CULTURE VESSEL FOR THREE-DIMENSIONAL CELL CULTIVATION AND THREE-DIMENSIONAL CELL CO-CULTIVATION METHOD USING SAME

(71) Applicants: KOREA INSTITUTE OF INDUSTRIAL TECHNOLOGY, Cheonan-si (KR); CEFO CO., LTD., Seoul (KR); KOREA RESEARCH INSTITUTE OF CHEMICAL TECHNOLOGY, Daejeon (KR); KOREA RESEARCH INSTITUTE OF STANDARDS AND SCIENCE, Daejeon (KR)

(72) Inventors: Dongmok Lee, Daegu (KR); Woojong Lee, Seoul (KR); Woojin Kim, Daegu (KR); Hyunsook Park, Seoul (KR); Sunray Lee, Seoul (KR); Kiyoung Kim, Daejeon (KR); Sungbum Park, Daejeon (KR); Kwangrok Kim, Daejeon (KR); Byumseok Koh, Daejeon (KR); Kyongjin Choi, Sejong (KR); Hyejin Nam, Daejeon (KR); Dukjin Kang, Daejeon (KR)

(73) Assignees: KOREA INSTITUTE OF INDUSTRIAL TECHNOLOGY, Cheonan-si (KR); CEFO CO., LTD., Seoul (KR); KOREA RESEARCH INSTITUTE OF CHEMICAL, Daejeon (KR); KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 302 days.

(21) Appl. No.: 16/640,849

(22) PCT Filed: Aug. 22, 2018

(86) PCT No.: PCT/KR2018/009688
§ 371 (c)(1),
(2) Date: Feb. 21, 2020

(87) PCT Pub. No.: WO2019/039875
PCT Pub. Date: Feb. 28, 2019

(65) Prior Publication Data
US 2021/0040425 A1 Feb. 11, 2021

(30) Foreign Application Priority Data
Aug. 22, 2017 (KR) .................... 10-2017-0106348
Aug. 21, 2018 (KR) .................... 10-2018-0097285

(51) Int. Cl.
*C12M 1/32* (2006.01)
*C12N 5/0775* (2010.01)

(52) U.S. Cl.
CPC .............. *C12M 1/32* (2013.01); *C12M 23/12* (2013.01); *C12N 5/0667* (2013.01);
(Continued)

(58) Field of Classification Search
CPC ....... C12M 1/32; C12M 23/12; C12N 5/0667; C12N 2502/1157; C12N 2502/1382; C12N 2513/00; C12N 2533/40
(Continued)

(56) References Cited

U.S. PATENT DOCUMENTS

2010/0151510 A1* 6/2010 Kanome ................ C12M 23/12
435/39

FOREIGN PATENT DOCUMENTS

JP    2005-176630 A    7/2005
JP    2006-280298 A    10/2006
(Continued)

OTHER PUBLICATIONS

International Search Report for PCT/KR2018/009688, dated May 22, 2019.

*Primary Examiner* — Michael L Hobbs
*Assistant Examiner* — Lenora A Abel
(74) *Attorney, Agent, or Firm* — Sughrue Mion, PLLC (57) ABSTRACT

The present invention relates to a culture vessel for three-dimensional cell cultivation and a three-dimensional cell co-cultivation method using the same. The culture vessel comprises a well formed by a column positioned thereon and at least one support protruding from the column within the well. In contrast to conventional techniques, the present
(Continued)

invention allows cells to be cultured at a position spaced from a culture vessel, thus enjoying the advantage of smoothly supplying oxygen necessary for three-dimensional cell culture structures.

8 Claims, 13 Drawing Sheets

(52) U.S. Cl.
CPC ............ *C12N 2502/1157* (2013.01); *C12N 2502/1382* (2013.01); *C12N 2513/00* (2013.01); *C12N 2533/40* (2013.01)

(58) Field of Classification Search
USPC ...................................... 435/299.2
See application file for complete search history.

(56) References Cited

FOREIGN PATENT DOCUMENTS

| | | |
|---|---|---|
| JP | 4632400 B2 | 2/2011 |
| JP | 2012-509663 A | 4/2012 |
| JP | 2013-215152 A | 10/2013 |
| JP | 2016-007179 A | 1/2016 |
| KR | 10-2015-0118279 A | 10/2015 |

* cited by examiner

FIG. 12B

CULTURE VESSEL FOR THREE-DIMENSIONAL CELL CULTIVATION AND THREE-DIMENSIONAL CELL CO-CULTIVATION METHOD USING SAME

CROSS REFERENCE TO RELATED APPLICATIONS

This application is a National Stage of International Application No. PCT/KR2018/009688 filed Aug. 22, 2018, claiming priority based on Korean Patent Application No. 10-2017-0106348 filed Aug. 22, 2017, and Korean Patent Application No, 10-2018-0097285 filed Aug. 21, 2018.

TECHNICAL FIELD

The present invention relates to a culture vessel for three-dimensional cell culture and a three-dimensional (3D) cell co-culture method using the same, and more particularly, unlike the prior art, to a culture vessel for 3D cell culture which facilitates a smooth supply of air required for a 3D cell culture structure by cultivating cells at a location spaced apart from the bottom surface of the culture vessel and a 3D cell co-culture method using the same.

BACKGROUND ART

Cell culture is the most basic research method in biotechnological research, and is very widely used to study human diseases as well as the functions of organisms. More than 40 years have passed since the common method for eukaryotic cell culture was developed and established, and the method which has been most frequently used to date for supporting the growth of adherent cells is culturing cells on a two-dimensional (2D) surface which is formed of a synthetic polymer resin such as polystyrene, polypropylene, polyethylene or polycarbonate (PC), or a substrate formed of glass.

However, since cells grown by a 2D cell culture method, which is a monolayer cell culture method, are grown attached to a culture vessel surface treated for cells to be easily attached, they are very different from cells grown in a 3D tissue environment. Therefore, since 2D and 3D cell cultures have overall morphological differences, and many complicated life phenomena, which take place by common 2D cell culture, for example, the expression of a receptor, the transcriptional regulation of genes, cell migration and apoptosis, are very different from those taking place in a real tissue environment, the 2D cell culture method has the problem of not accurately reflecting the physiological environment of an organism in which cells are grown in three dimensions.

Actually, in the development of therapeutic agents for metabolic diseases such as obesity, diabetes, arteriosclerosis, etc., there are many difficulties in developing new drugs, for example, a great decrease in efficacy in an in vivo animal experiment from excellent efficacy exhibited in an early in vitro experiment. To solve such a problem, an in vitro model which is similar to an in vivo model capable of predicting accurate efficacy and toxicity of a drug at the early stage of developing a therapeutic agent is required.

Because of spatial limitations during 3D cell culture, it is difficult for conventional cell culture vessels to achieve sufficient 3D cell growth and tissue formation due to poor air supply and circulation, and thus there is difficulty in applying them to drug screening or toxicity testing.

Therefore, to solve such a problem, the development of technology for cell culture vessels which are suitable for rapid growth of 3D cells and enable 2D and 3D co-culture is required.

DISCLOSURE

Technical Problem

The present invention is provided to solve the above-described problems, and unlike the prior art, directed to providing a culture vessel for 3D cell culture which facilitates a smooth supply of air required for a 3D cell culture structure by cultivating cells at a location spaced apart from the bottom surface of the culture vessel and a 3D cell co-culture method using the same.

The insertion and acquisition and removal of a 3D structure may be easily achieved by implementing the structure of a support separately supporting the 3D structure on the culture vessel.

In addition, due to the support structure optimized for 3D culture, air circulation and a smooth supply of nutrients into media can be achieved, and thus may be effectively maintained in co-culture of two or more types of cells as well as 3D cell culture.

With the 3D cell culture method according to the present invention, rapid growth of cells and various size adjustments are possible, and the 3D cultured and differentiated cells may be applied to an animal alternative method to be effectively used in drug screening or toxicity testing.

In addition, the present invention is directed to providing a culture vessel for 3D cell culture with high durability, in which a support region is designed to be concave to prevent an external contraction caused by a support projecting from a column and a 3D cell co-culture method using the same.

In addition, the culture vessel may be used as a container for 3D cell culture and differentiation or tissue culture for restoring functions of damaged human tissue.

Technical Solution

The culture vessel for 3D cell culture according to the present invention for achieving the above-described objects may include a well formed by a column located on the bottom surface of the culture vessel, and at least one support projecting from the column in the well.

The support may be spaced apart from the bottom surface of the culture vessel and located at 20 to 60% of the height of the column.

Alternatively, the support may be supports formed along the side surface of the column while coming into contact with the bottom surface of the culture vessel. Here, the uppermost part of the support may be located at 20 to 60% of the height of the column from the culture vessel.

In the culture vessel for 3D cell culture according to the present invention, based on the cross-section of the well, the distance from the column to the end of the support may be 15 to 30% with respect to the diameter of the well.

In addition, at least a part of the column region contacting the support and at least a part of the support region contacting the column region may be removed.

In addition, the culture vessel for 3D cell culture according to the present invention may include a well formed by a column located on the bottom surface of the culture vessel and at least one support projecting from the bottom surface of the culture vessel, wherein at least a part of the top surface of the support may be concave. The top surface of the support is divided into an edge region and a center region, in which the center region is concave, the edge region may be flat or project convexly in a projecting direction, and the edge region may account for 10 to 30% of the top surface of the support, and the center region may account for 70 to 90% thereof.

The top of the support may be formed in a curved shape, and the uppermost part of the support may be located at 20 to 60% of the height of the column.

In addition, the 3D cell co-culture method according to the present invention may include a preparation step of preparing a culture vessel for 3D cell culture which includes at least one support projecting from a column or the bottom surface inside a well formed by a column located on the bottom surface of the culture vessel; an inoculation step of inoculating first cells in the well; an exchanging step of, after culturing the first cells, removing a supernatant and at least partially exchanging a medium; and a co-culturing step of culturing a 3D structure inoculated with second cells on the support to co-culture.

After the co-culturing step, an exchanging step of changing the medium at intervals of 1 to 5 days.

Advantageous Effects

According to a culture vessel for 3D cell culture according to the present invention and a 3D cell co-culture method using the same, unlike the prior art, cells are cultivated at a position spaced apart from the bottom surface of the culture vessel, and thus oxygen required for a 3D cell culture structure can be easily supplied.

By implementing a support structure for separately supporting the 3D structure on the culture vessel, the 3D structure can be easily inserted, acquired and removed.

In addition, due to the support structure optimized for 3D culture, the co-culture of two or more types of cells, as well as the 3D cell culture, can be effectively performed.

The 3D cell culture method according to the present invention enables rapid growth of cells and various size adjustments, and can be applied to a biomimetic model or an animal alternative method to be effectively used in drug screening or efficacy confirmation, or toxicity testing.

In addition, the culture vessel can have high durability by designing a support region to be concave to prevent an external contraction caused by a support projecting from a column.

In addition, the culture vessel can be used as a 3D cell culture or tissue culture vessel for restoring functions of damaged human tissue.

DESCRIPTION OF DRAWINGS

FIGS. 12A and 12B illustrate an exemplary embodiment of the culture vessel for 3D cell culture according to the present invention, in which

MODES OF THE INVENTION

Hereinafter, preferable embodiments of a culture vessel for 3D cell culture according to the present invention and a 3D cell co-culture method using the same will be described in detail with reference to the accompanying drawings. The present invention may be better understood by the following examples, which are merely provided to exemplify the present invention are not intended to limit the scope of the present invention defined by the accompanying claims.

Figure 1:
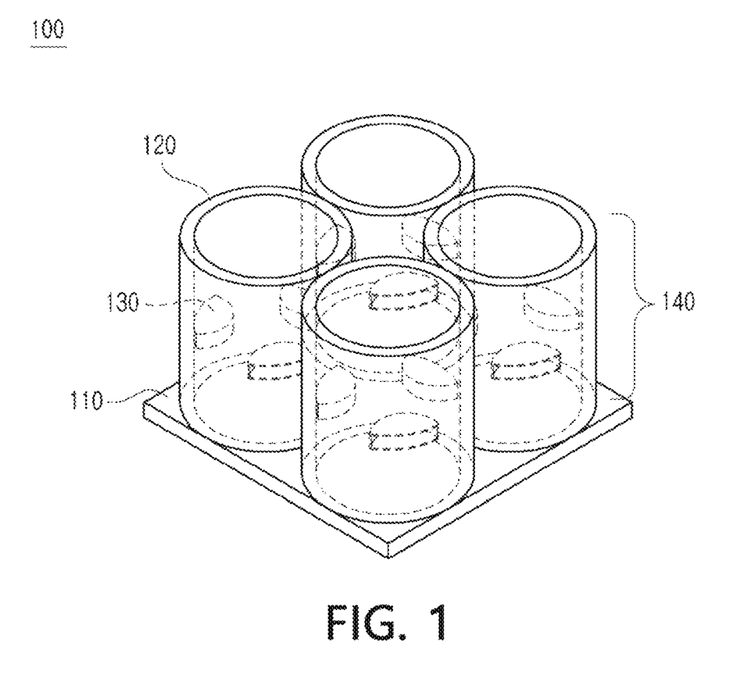
FIG. 1 is a perspective view illustrating a first example of a culture vessel for 3D cell culture according to the present invention.
Figure 2:
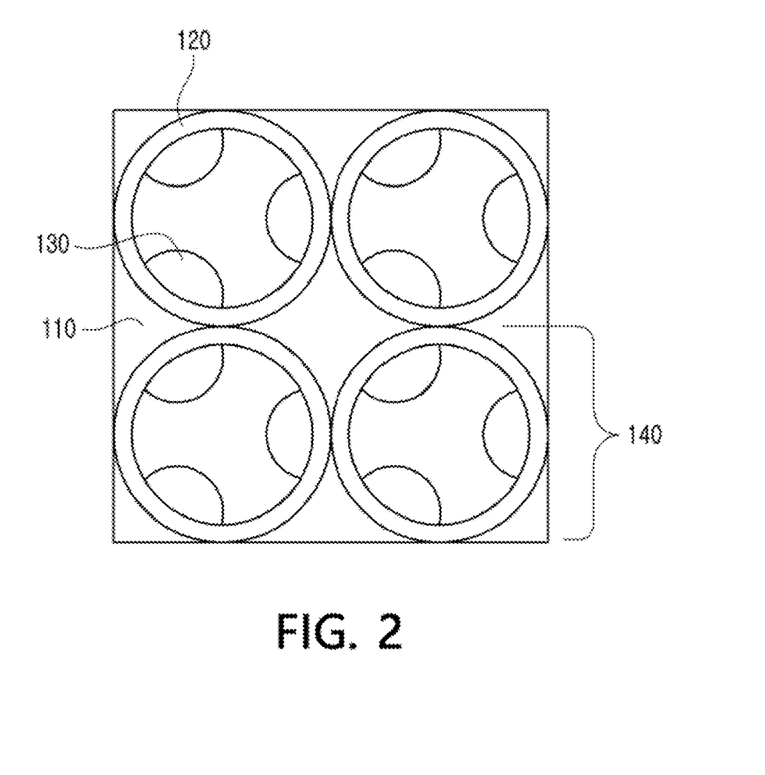
FIG. 2 is a plan view illustrating a first example of a culture vessel for 3D cell culture according to the present invention.

As shown in FIGS. 1 and 2, the first example of the culture vessel for 3D cell culture 100 according to the present invention may include a well 140 formed by a column 120 located on the bottom surface 110 of the culture vessel, and at least one support 130 projecting from the column 120 in the well 140.

First, the bottom surface 110 of the culture vessel is a surface forming the base, and may be formed of any material applied to cell culture, for example, polystyrene (PS), polypropylene (PP), polyethylene (PE), polycarbonate or glass.

Figure 4:
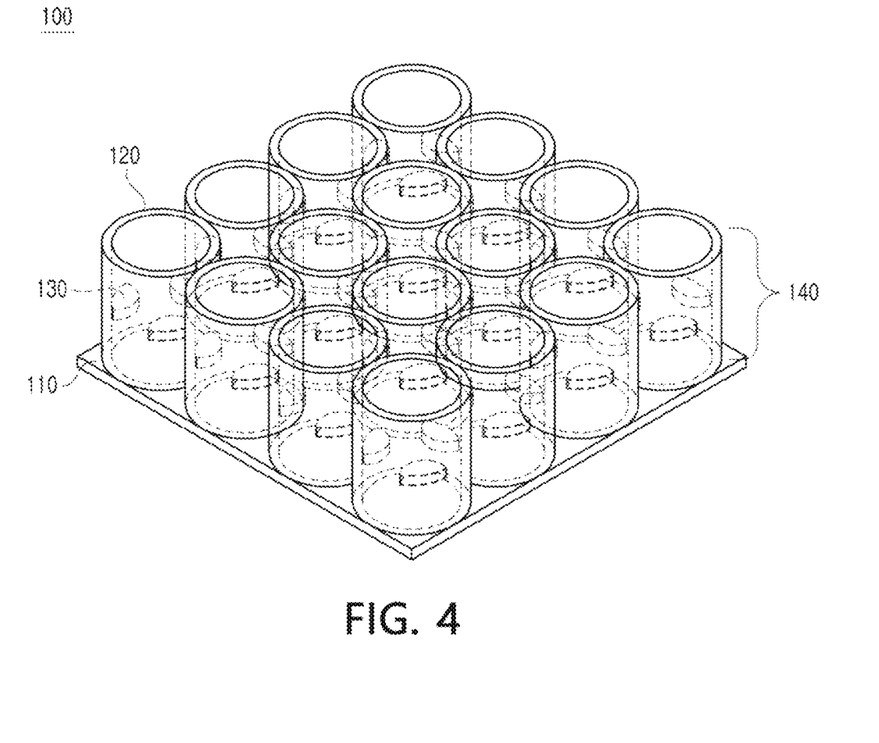
FIG. 4 is a perspective view illustrating a 16-well culture vessel for 3D cell culture.

The column 120 may be formed in contact with the bottom surface 110 of the culture vessel, preferably formed of the same material as the bottom surface 110, and integrally injection-molded. A plurality of the columns 120 may be located on the bottom surface 110 of one culture vessel, and one well 140 may be formed per column 120. As shown in FIG. 4, the culture vessel may be formed to have various number of wells, for example, 16 or 96 wells.

The cross-sectional shape of the column 120 may be a circular or polygonal shape, preferably, an oval or circular shape, and most preferably, a circular shape.

The support 130 may be spaced apart from the bottom surface 110 of the culture vessel, and thus it is effective that the support 130 is preferably located at 20 to 60%, more preferably 25 to 50%, and most preferably 30 to 35% of the height of the column 120 from the bottom surface. When the support 130 is located lower than 20% of the height of the column 120, it is difficult to achieve smooth air circulation and supply to cells in the lower part of the culture vessel, and when the support 130 is located higher than 60% of the height of the column 120, it is difficult to achieve co-culture of a 3D cell structure loaded on the support 130 and other cells contained in a well 140.

In addition, as shown in FIG. 2, based on the cross-section of the well 140, the distance from the column 120 to the end of the support 130 may be 15 to 30% with respect to the diameter of the well 140, and it is effective that the distance from the column 120 to the end of the support 130 is preferably 20 to 25%, and most preferably, 22 to 23%. When the distance is less than 15%, it is difficult to stably support the 3D cell structure, and when the distance is more than 30%, the effect of spacing the support 130 from the bottom surface 110 is lowered, and in other words, the difficulty in smooth air circulation and supply has an adverse effect on cell growth.

It is effective that the number of the supports 130 is preferably 2 to 5, more preferably, 3 to 4, and most preferably 3. When the number of the supports 130 is less than 2, it is actually impossible to support the 3D cell structure, and when the number of the supports 130 is more than 5, an open space between the support 130 and the bottom surface 110 of the culture vessel is so narrow that effects such as the air circulation and supply, and co-culture of two or more types of cells are significantly decreased.

Figure 3:
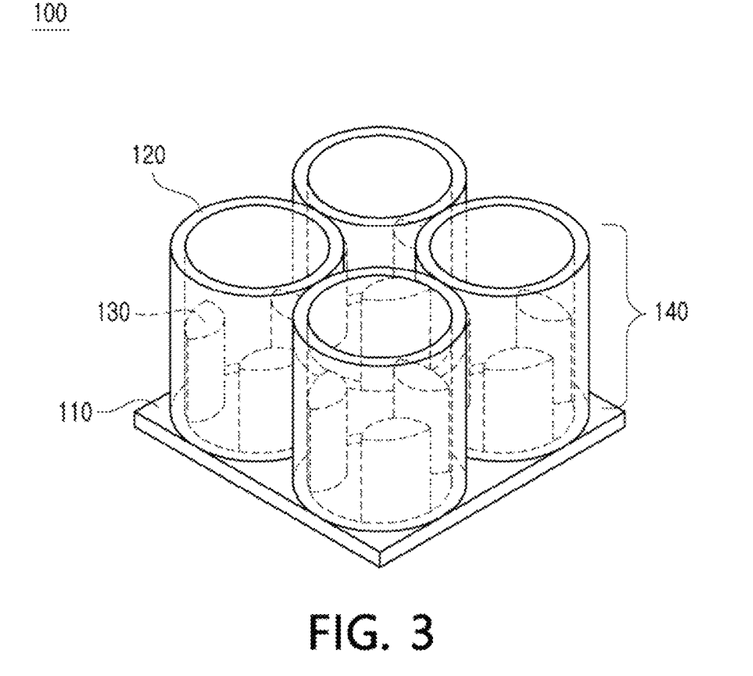
FIG. 3 is a perspective view illustrating a second example of a culture vessel for 3D cell culture according to the present invention.

As shown in FIG. 3, in the second example of the culture vessel for 3D cell culture 100 according to the present invention, the support 130 may be formed along the side surface of the column 120 in contact with the bottom surface 110 of the culture vessel.

As such, since the support 130 is formed along the side surface of the column 120 from the bottom surface 110 of the culture vessel, the support 130 and the column 120 may be easily integrally injection-molded, a production process may be simplified, and economic feasibility may be increased. Moreover, since the support 130 is formed in a column shape along the side surface of the column 120, the culture vessel has much higher stability and durability.

Here, it is effective that the uppermost part of the support 130 is located at 20 to 60%, preferably 25 to 50%, and most preferably, 30 to 35% of the height of the column 120 from the bottom surface 110 of the culture vessel. When the uppermost part of the support 130 is located lower than 20% of the height of the column 120, it is difficult to achieve active oxygen supply to cells in the lower part of the culture vessel, and when the uppermost part of the support 130 is located higher than 60%, it is difficult to achieve co-culture between a 3D cell structure located on the support 130 and other cells contained in the well 140.

Figure 5:
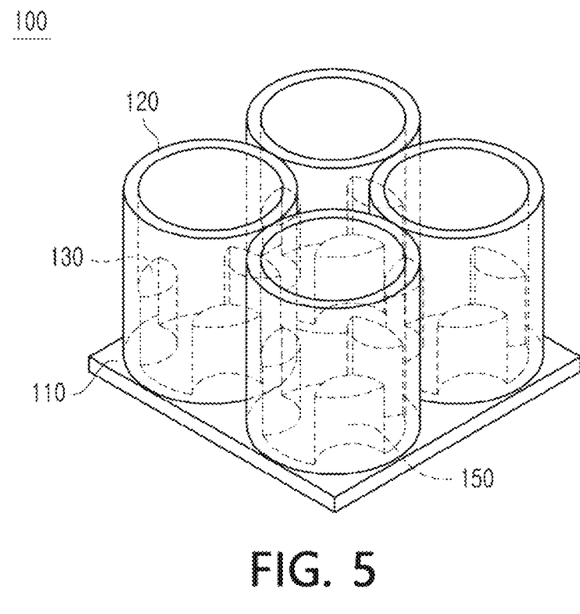
FIG. 5 is a perspective view illustrating a third example of a culture vessel for 3D cell culture according to the present invention.
Figure 6:
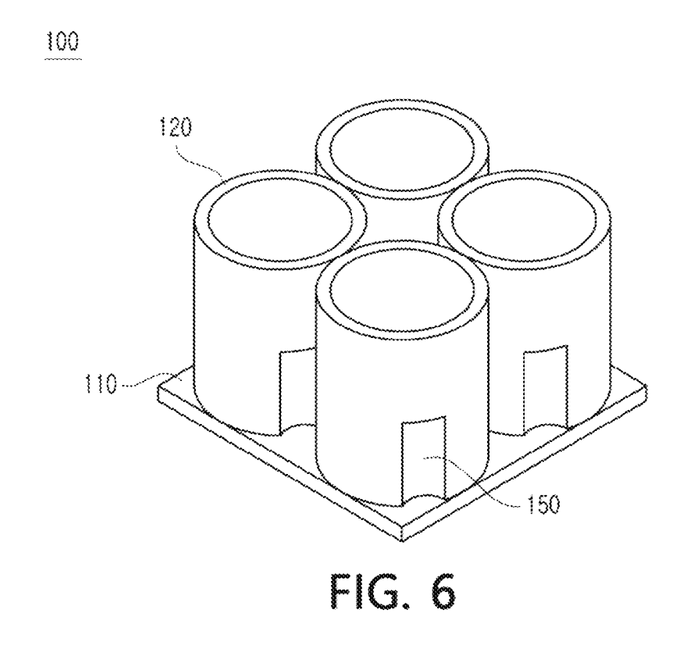
FIG. 6 is an external view illustrating a third example of a culture vessel for 3D cell culture according to the present invention.

As shown in FIGS. 5 and 6, in the third example of the culture vessel for 3D cell culture 100 according to the present invention, at least a part of the column 120 region in contact with the support 130 and at least a part of the support 130 region in contact with the column 120 region may be removed.

Here, a partial region removed from the support 130 and a partial region removed from the column 120 in contact with the support 130 are undercut regions 150 as shown in FIGS. 5 and 6, and it is preferable that other regions except the surface of the support 130 formed in the well 140 are entirely removed.

Figure 7:
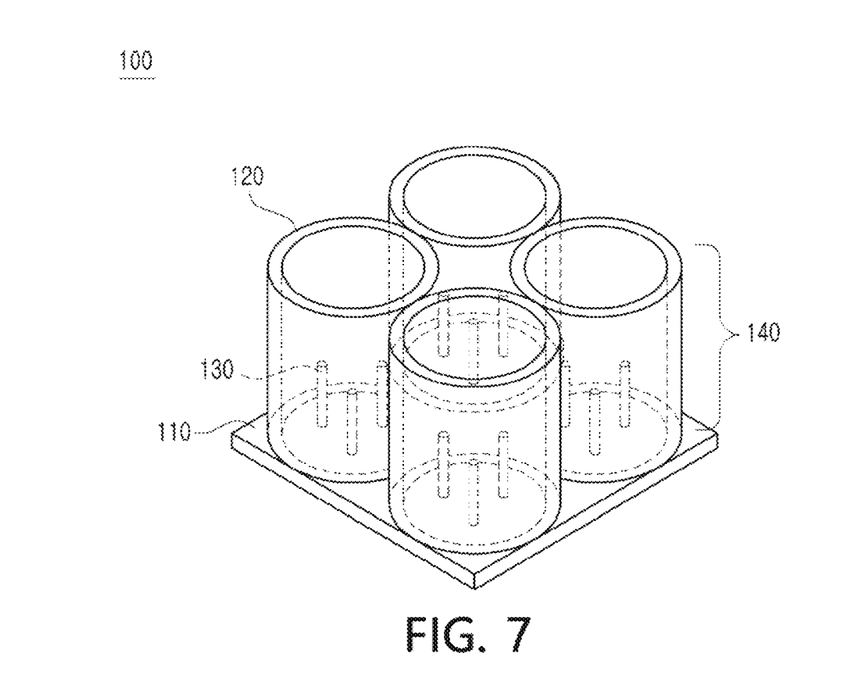
FIG. 7 is a perspective view illustrating a fourth example of a culture vessel for 3D cell culture according to the present invention.
Figure 8:
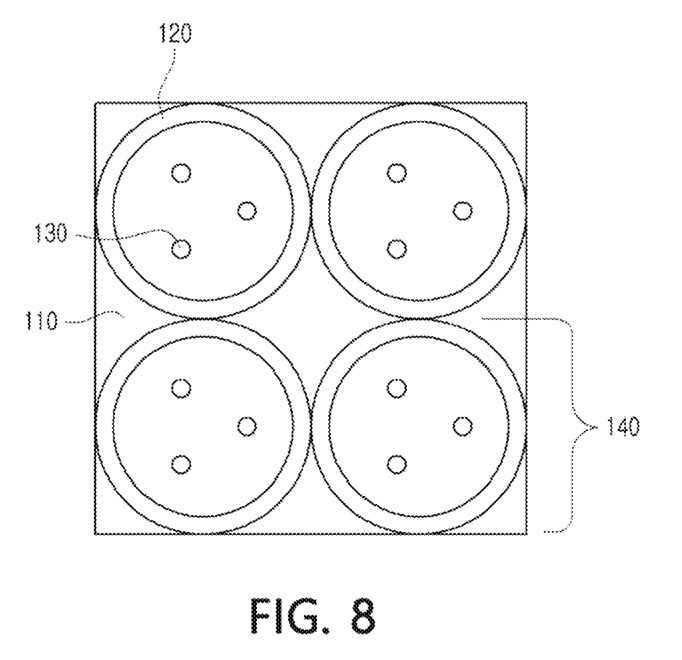
FIG. 8 is a plan view illustrating a fourth example of a culture vessel for 3D cell culture according to the present invention.

In addition, as shown in FIGS. 7 and 8, in the fourth example of the culture vessel for 3D cell culture 100 according to the present invention, a well 140 may be formed by a column 120 located on the bottom surface 110 of a column vessel, and at least one support 130 projecting from the bottom surface 110 of the culture vessel may be included in the well 140. As the support 130 is projecting from the bottom surface 110 of the culture vessel, rather than the column 120, a 3D cell structure is spaced apart from the bottom surface 110 of the culture vessel.

It is effective that the uppermost part of the support 130 is preferably located at 20 to 60%, more preferably, 25 to 50%, and most preferably, 30 to 35% of the height of the column 120 from the bottom surface 110 of the culture vessel. When the uppermost part of the support 130 is located lower than 20% of the height of the column 120, it is difficult to actively supply oxygen to cells in the lower part of the culture vessel, and when the uppermost part of the support 130 is located higher than 60% of the height of the column 120, it is difficult to achieve co-culture between a 3D cell structure loaded on the support 130 and other cells contained in a well 140.

As shown in FIG. 8, based on the cross-section of the well 140, it is effective that the diameter of the support 130 is preferably 2 to 10%, more preferably, 4 to 8%, and the most preferably 5 to 6% of the diameter of the well 140. When the diameter of the support 130 is less than 2%, it is difficult to stably support the 3D cell structure, and when the diameter of the support 130 is more than 10%, an effect of spacing the support 130 from the bottom surface 110 of the culture vessel is lowered, and in other words, it is difficult to achieve smooth air circulation and supply nutrients, which may adversely affect cell growth.

Figure 9:
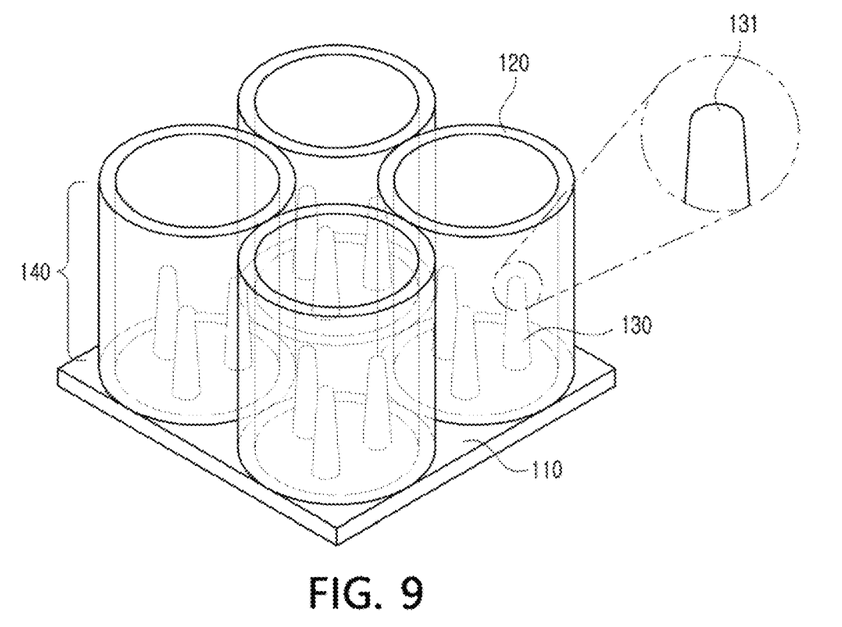
FIG. 9 is a plan view illustrating a fifth example of a culture vessel for 3D cell culture according to the present invention.

In addition, as shown in FIG. 9, in the fifth example of the culture vessel for 3D cell culture 100 according to the present invention, the upper end of the support 130 may be configured as a curved surface 131. By forming the curved surface, cell damage caused by an angular region may be prevented, and the cell-inoculated 3D structure may be more stably supported, resulting in increased viability.

Figure 10:
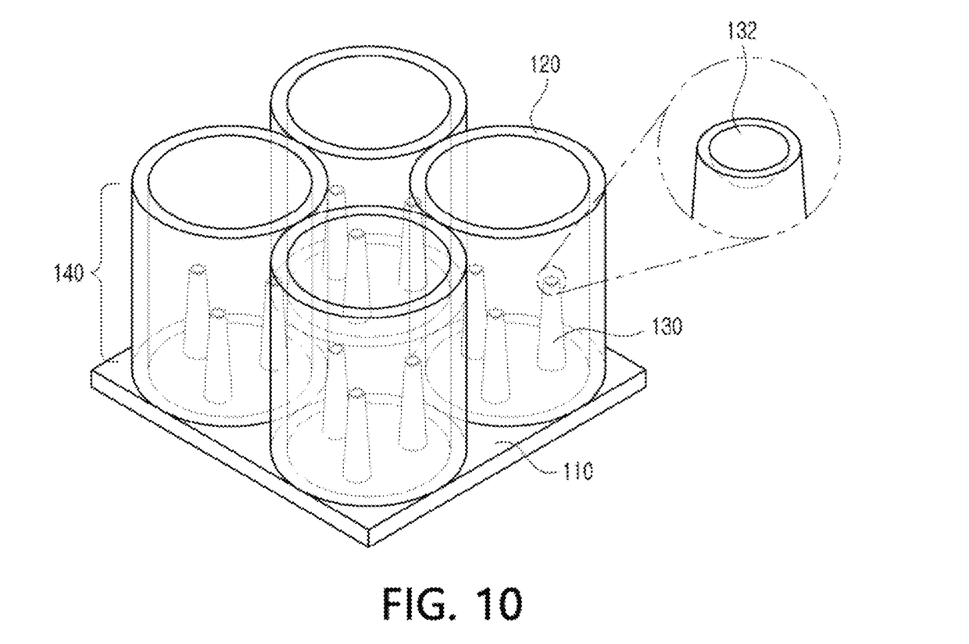
FIG. 10 is a plan view illustrating a sixth example of a culture vessel for 3D cell culture according to the present invention.

As shown in FIG. 10, in the sixth example of the culture vessel for 3D cell culture 100 according to the present invention, at least a part of the top surface of the support 130 may be concave. Since the center of the top end of the support 130 is recessed most deeply, cell support is more stable, and thus co-culture efficiency and viability may be significantly improved. In addition, since the surface where cells contact with the support 130 is minimized and which is concave can maximize the smooth air circulation effect, it is effective in cell growth.

The top surface of the support 130 is divided into an edge region and a center region 132, in which the center region 132 is concave, and the edge region may be flat or projecting convexly in a projecting direction. As cells only contact the edge region, the culture vessel has advantages that cell damage is minimized and cell viability is greatly increased by smooth air circulation.

The edge region may account for 10 to 30% of the top surface of the support, the center region may account for 70 to 90% thereof, and it is effective that the edge region preferably accounts for 15 to 20%, and the center region preferably accounts for 80 to 85%. This is the optimized area range obtained through several experiments to provide an optimal area for stably supporting cells and increasing cell growth and viability as high as possible.

Subsequently, the 3D cell culture method according to the present invention may include a preparation step (S10); and a culturing step (S11). This is a method capable of effectively culturing cells using the structure of a culture vessel for 3D cell culture according to the present invention.

First, the preparation step (S10) is a step of preparing a culture vessel for 3D cell culture which includes at least one support projecting from a column in a well formed by the column located on the bottom surface of the culture vessel or at least one support projecting from the bottom surface of the culture vessel. In the preparation step (S10), the uppermost part of the support may be located at 20 to 60% of the height of the column from the column or the bottom surface of the culture vessel.

The culturing step (S11) is a step of culturing a cell-inoculated 3D structure placed on the support. Due to the support structure optimized for 3D culture, the 3D cell culture progresses efficiently.

In addition, the 3D cell co-culture method according to the present invention may include a preparation step (S20); an inoculation step (S21); an exchanging step (S22); and a co-culturing step (S23). This is the method for effectively co-culturing first cells and second cells using the structure of the culture vessel for 3D cell culture according to the present invention.

First, the preparation step (S20) is a step of preparing a culture vessel for 3D cell culture, which includes at least one support projecting from a column in a well formed by the column located on a culture vessel or at least one support projecting from the bottom surface of the culture vessel. In the preparation step (S20), the uppermost part of the support may be located at 20 to 60% of the height of the column from the column or the bottom surface of the culture vessel.

The inoculation step (S21) is a step of inoculating first cells into the well. That is, the first cells and a medium may be inoculated into the well.

Here, the first cells may be any cells that can be co-cultured with second cells, and particularly, at least one of adherent cells, mesenchymal or mesenchymal stem cells, preadipocytes, adipocytes, smooth muscle cells (SMCs) and macrophages.

The exchanging step (S22) is a step of removing a supernatant after culturing the first cells and at least partially exchanging a medium. Co-culture efficiency may be increased by removing a supernatant generated by the first cell culture in the medium contained in the well and partially or entirely exchanging the medium.

The co-culturing step (S23) is a step of co-culturing a second cell-inoculated 3D structure located on the support. Here, the 3D structure is preferably in the form of a bead or support.

Here, the second cells may be eukaryotic cells that can be cultured, and more particularly, at least one of epithelial cells, fibroblasts, osteoblasts, chondrocytes, hepatocytes, cord blood cells, umbilical cord mesenchymal stem cells (UCMSCs), adipose-derived mesenchymal stem cells (ADMSCs) or bone marrow-derived mesenchymal stem cells (BMMSCs).

Finally, the exchanging step (S24) is a step of exchanging the medium at intervals of 1 to 5 days after the co-culturing step (S23). More preferably, it is effective that the medium is exchanged at intervals of 2 to 3 days. This is to continuously grow cells or tissue by removing a cell survival-inhibiting material produced during the supply of nutrients required for cell culture and culture.

EXAMPLES

Example 1) Manufacture of Culture Vessel and Sterilization

As an example of the present invention, a culture vessel was manufactured by 3D printing technology for manufacturing a shape by layering through solid freeform fabrication (SFF) using a rapid prototyping (RP) device, and sterilization was performed using an electron beam accelerator.

Example 2) Culturing of First Cells

To measure an effect of 3D cell culture using the culture vessel for 3D cell culture according to the present invention, an experiment was performed under the following conditions.

Cells: 3T3-L1 (preadipocytes) ($2.45 \times 10^6$ cells/5 mL/Tube), ADMSCs

Culture period: 7 days

Cell count: counted on Day 0, 3, 7

Mixed alginate: 1.3% concentration

First cells were 3T3-L1 (preadipocytes), and specifically, frozen first cells were thawed in a 37° C. constant-temperature water bath and transferred to a 15 ml tube and then centrifuged at 1,500 rpm for 5 minutes after adding a basic medium (DMEM+1% antibiotics), and the supernatant was removed. With the addition of the basic medium again, the above-described method was repeated to completely remove a cryoprotective component, and then the cells were inoculated in a 100 mm culture dish with a medium containing DMEM+1% antibiotics+10% FBS and cultured in a 37° C., 5% $CO_2$ incubator. Four to five days later, when the cells were sufficiently proliferated, the cells were treated with 0.05% trypsin-EDTA, and inoculated at a concentration of $1 \times 10^3$ into each well of the culture vessel.

Example 3) Manufacture of Beads Containing Second Cells

Second cells were ADMSCs, and a second cell-inoculated 3D structure was prepared in a bead form.

The beads were prepared by a melting step of melting components at 65° C. after a medium, an alginate and gelatin were input into a tube; a stirring step of lowering the temperature of the tube to 37° C., inputting the second cells ($2.45 \times 10^6$ cells/5 mL/tube) into the tube, and then stirring the tube at 500 rpm for 2 minutes; and a preparation step of forming the mixture in the tube in the form of beads and adding the beads to a calcium chloride solution for crosslinking.

After stirring, bubbles were removed by performing centrifugation at 1500 rpm. In the preparation step, the concentration of the calcium chloride solution was 5%.

The crosslinked beads were washed with phosphate buffered saline (PBS), and added to a medium containing 10% fetus bovine serum (FBS) and incubated in a 37° C., 5% $CO_2$ incubator, thereby preparing the second cell-inoculated 3D structure in a bead form.

Example 4) Manufacture of Support and Sterilization Process

A support was manufactured using polycaprolactone. First, polycaprolactone was put into a tube, pressurized at 90° C. and 650 to 730 kPa, and then a 3D support was manufactured using an intake function of an air controller and a sterilization process was performed using electron beam acceleration.

Example 5) 3D Cell Culture Using Support Containing Second Cells

For 3D cell culture using a second cell-inoculated support, 25 μL of second cells were inoculated on each of four drop supports and incubated for 1 hour, 1 mL of a medium was added, and then the cells were incubated at 37° C. under 5% carbon dioxide, thereby preparing a 3D structure in the form of the second cell-inoculated support.

Figure 11:
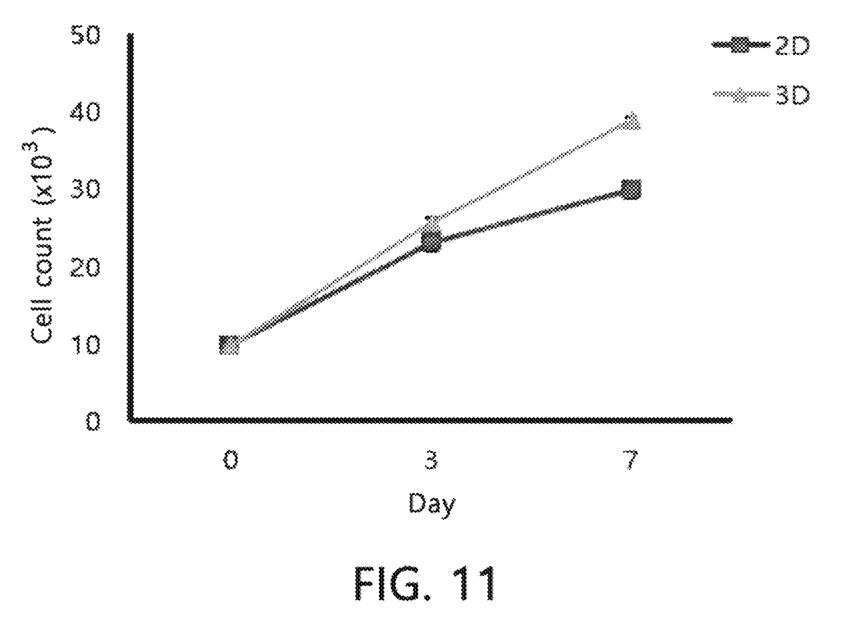
FIG. 11 is a graph illustrating an experimental result of 3D cell culture using a culture vessel for 3D cell culture according to the present invention.
Figure 12A:
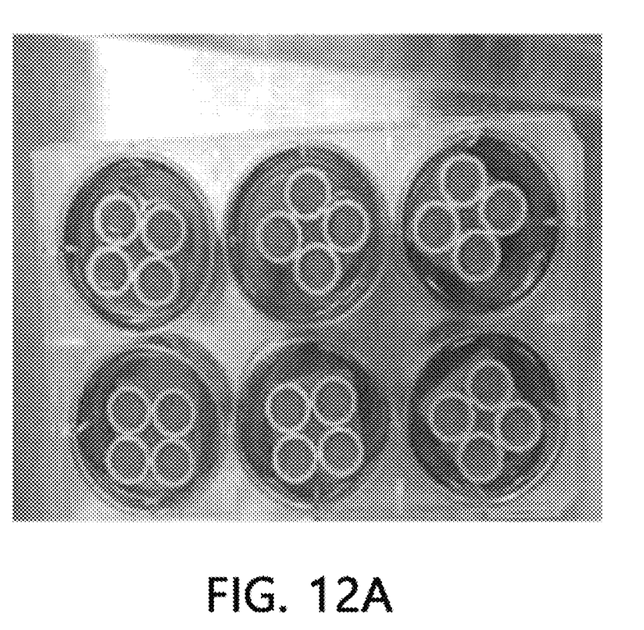
FIG. 12A is an image illustrating that beads containing cells are cultured in the implemented culture vessel.
Figure 12B:
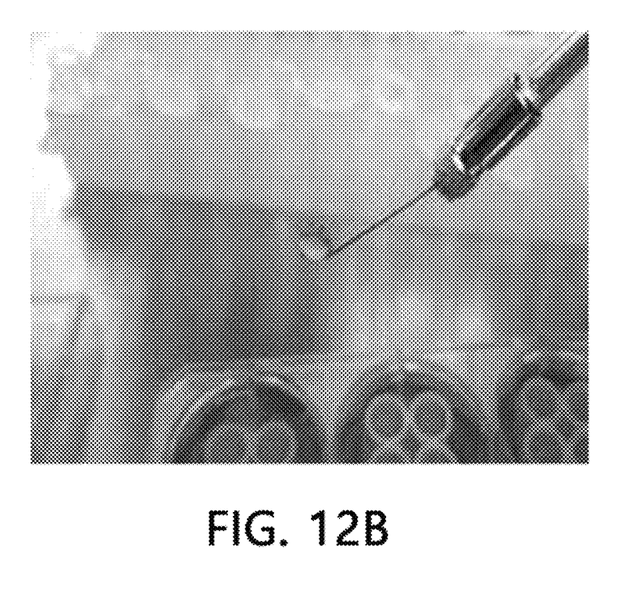
FIG. 12B is an image illustrating the beads containing cells are acquired from the culture vessel.

Referring to FIGS. 11, 12A and 12B, it can be seen that, as culture time passes, in the 3D cell culture performed using the culture vessel according to the present invention, compared with 2D cell culture using a common culture vessel, a cell count may be increased, rather than decreased. That is, it can be confirmed from an actual experiment that, by using the culture vessel according to the present invention, 3D cell culture can be more persistently performed.

Exemplary embodiments of the present invention were described above, but the present invention can use various changes, modifications and equivalents. It is clear that, in the present invention, the embodiments can be suitably modified and applied in the same manner. Therefore, the descriptions do not limit the scope of the present invention as defined by the limitations of the accompanying claims.

INDUSTRIAL APPLICABILITY

The present invention relates to a culture vessel for 3D cell culture and a 3D cell co-culture method using the same.

The invention claimed is:

1. A culture vessel for three-dimensional (3D) cell culture based on a support for a three-dimensional structure inoculated with cells, comprising:
a well formed by a column located on a bottom surface of a culture vessel; and
three or four supports spaced from each other in the well and projecting from an inner wall of the column in the well,
wherein an uppermost part of each support is located at the same height as each other and located at 20 to 60% of a height of the column so that it is configured to support the three-dimensional structure, and the three-dimensional structure is spaced apart from the bottom surface when the three-dimensional structure is inserted into the well, and
wherein a hollow area is provided between the three or four supports, and the three-dimensional structure is located in the hollow area.

2. The culture vessel of claim 1, wherein the respective support is spaced apart from the bottom surface of the culture vessel.

3. The culture vessel of claim 1, wherein the respective support is formed in contact with the bottom surface of the culture vessel, and formed along a side surface of the column.

4. The culture vessel of claim 1, wherein, based on a cross-section of the well, a distance from the column to the end of the respective support is 15 to 30% with respect to a diameter of the well.

5. The culture vessel of claim 3, wherein at least a part of the column in contact with the respective support and at least a part of the respective support in contact with the column are removed.

6. A culture vessel for three-dimensional (3D) cell culture based on a support for a three-dimensional structure inoculated with cells, comprising:
a well formed by a column located on the bottom surface of a culture vessel; and
three or four supports spaced apart from each other in the well and projecting from the column in the well,
wherein at least a part of a top surface of the respective support is formed in a concave shape,
wherein an uppermost part of each support is located at the same height as each other and located at 20 to 60% of a height of a column so that it is configured to support the three-dimensional structure, and the three-dimensional structure is spaced apart from the bottom surface when the three-dimensional structure is inserted into the well, and
wherein a hollow area is provided between the three or four supports, and the three-dimensional structure is located in the hollow area.

7. The culture vessel of claim 6, wherein the top surface of the respective support is divided into an edge region and a center region, in which the center region is concave, the edge region is flat or projecting convexly in a projecting direction, and the edge region account for 10 to 30% of the top surface of the respective support and the center region accounts for 70 to 90% thereof.

8. The culture vessel of claim 6, wherein the top surface of the respective support is formed in a curved shape.

* * * * *